(12) United States Patent
Palmer et al.

(10) Patent No.: US 8,519,867 B2
(45) Date of Patent: Aug. 27, 2013

(54) METHOD AND SYSTEM FOR REDUCING TRANSMITTER POWER CONSUMPTION WHILE AVOIDING DELAY OF DISPLAYED INFORMATION

(75) Inventors: Michael J. Palmer, New Berlin, WI (US); Matthew Grubis, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 496 days.

(21) Appl. No.: 12/977,675

(22) Filed: Dec. 23, 2010

(65) Prior Publication Data
US 2012/0161959 A1 Jun. 28, 2012

(51) Int. Cl.
*G08C 19/16* (2006.01)

(52) U.S. Cl.
USPC .......... 340/870.01; 340/870.07; 340/2.1; 600/522; 128/903; 607/16; 607/30

(58) Field of Classification Search
USPC ....... 340/870.01, 870.07; 600/522; 128/903; 607/16, 30, 60
See application file for complete search history.

(56) References Cited

U.S. PATENT DOCUMENTS

| 3,378,641 | A | 4/1968 | Varsos |
| 3,631,520 | A | 12/1971 | Atal |
| 4,719,642 | A | 1/1988 | Lucas |
| 2010/0141423 | A1 | 6/2010 | Lin et al. |

FOREIGN PATENT DOCUMENTS

| WO | 03065887 A1 | 8/2003 |
| WO | 2005057175 A2 | 6/2005 |

OTHER PUBLICATIONS

Search Report from corresponding GB Application No. 1121227.1 Apr. 5, 2012.

*Primary Examiner* — Daniel Wu
*Assistant Examiner* — Frederick Ott
(74) *Attorney, Agent, or Firm* — Andrus, Sceales, Starke & Sawall, LLP

(57) ABSTRACT

The system and method of the present application includes a wireless transmitter adapted to receive physiological signals from a patient and to wirelessly transmit the physiological signals to a receiver, where a display device prepares the physiological signal for display on a display monitor. In one embodiment, both the wireless transmitter and receiver further include an estimation algorithm module. The estimation algorithm module in each of the wireless transmitter and the receiver calculate a physiological signal based on a collected signal. The system displays the calculated, estimated signal unless the error of the estimated signal reaches a predetermined threshold. When the estimated signal is being displayed, no transmission from the wireless transmitter is necessary.

22 Claims, 3 Drawing Sheets

METHOD AND SYSTEM FOR REDUCING TRANSMITTER POWER CONSUMPTION WHILE AVOIDING DELAY OF DISPLAYED INFORMATION

FIELD

The present application is directed to the field of patient monitoring and wireless telemetry systems. More specifically, the present application is directed to the field of signal delay and power consumption in patient monitoring systems.

BACKGROUND

Many tradeoffs are encountered in the design of wireless patient monitoring systems. In particular, system characteristics related to data transmission such as time from acquisition to display of physiological signals are typically compromised in favor of lower power consumption in a battery-powered wireless transmitter. Such systems usually include an acquisition device, for example, a set of ECG leads coupled with a small, battery-powered transmitter that may be worn or attached to the patient or the patient's bed.

Such acquisition devices and transmitters have a limited power supply, for example, from a battery, and such wireless transmission uses a considerable amount of power in transmitting the physiological signals collected by the acquisition device to a receiver for display. Some of these systems add delay in order to conserve power by collecting and briefly storing physiological signals and therefore transmitting them less often than with a comparable wired connection. However, adding delay may not be satisfactory for the user.

In addition to performance tradeoffs, the design of a wireless patient monitoring system must take into account important safety considerations, such as timely delivery of information and alerts, and the accuracy of signals presented. It is necessary for the device to implement mitigations to prevent the occurrence of these hazards.

SUMMARY

The system and method of the present application includes a wireless transmitter adapted to receive physiological signals from a patient and to wirelessly transmit the physiological signals to a receiver, where a display device prepares the physiological signal for display on a display monitor. In one embodiment, both the wireless transmitter and receiver further include an estimation algorithm module. The estimation algorithm module in each of the wireless transmitter and the receiver calculate a physiological signal based on a collected signal. The system displays the calculated, estimated signal unless the error of the estimated signal compared to the actual signal reaches a predetermined threshold. When the estimated signal is being displayed, no transmission from the wireless transmitter is necessary.

In one aspect of the present application, a wireless physiological signal transmission and display system comprises a wireless transmitter in close proximity to a patient, the wireless transmitter including a transmission buffer module, and a first estimation algorithm module, wherein the wireless transmitter receives a physiological signal collected from the patient and calculates a first estimated signal with the first estimation algorithm module and compares the first estimated signal with the received physiological signal in real time, a receiver including a second estimation algorithm and a prioritized OR module, wherein the wireless transmitter wirelessly transmits the received physiological signal to the receiver and the second estimation algorithm module calculates a second estimated signal with the received physiological signal, a display device, wherein the prioritized OR module sends the received physiological signal to the display device as long as the received physiological signal is transmitted to the receiver, and further wherein when the first estimation algorithm module calculates the first estimated signal, and the first estimated signal is within a predetermined error range of the received physiological signal, the wireless transmitter stops transmitting the received physiological signal to the receiver, and the prioritized OR module sends the second estimated signal to the display device.

In another aspect of the present application, a method of wireless physiological signal transmission and display comprises receiving a physiological signal collected from a patient with a wireless transmitter in close proximity to the patient, the wireless transmitter including a transmission buffer module, and a first estimation algorithm module, calculating a first estimated signal with the first estimation algorithm module, comparing the first estimated signal with the received physiological signal in real time, wirelessly transmitting the received physiological signal to a receiver including a second estimation algorithm and a priority OR module, calculating a second estimated signal in the second estimated algorithm with the received physiological signal, sending the received physiological signal to a display device with the prioritized OR as long as the received physiological signal is transmitted to the receiver, wherein when the first estimation algorithm module calculates the first estimated signal, and the first estimated signal is within a predetermined error range of the received physiological signal, the wireless transmitter stops transmitting the received physiological signal to the receiver, and the prioritized OR module sends the second estimated signal to the display device.

In another aspect of the present application, a wireless physiological signal transmission and display system comprises a wireless transmitter in close proximity to a patient, the wireless transmitter including a transmission buffer module, wherein the wireless transmitter receives a physiological signal collected from a patient, a receiver including an estimation algorithm and a prioritized OR module, wherein the wireless transmitter wirelessly transmits the received physiological signal to the receiver and the estimation algorithm module calculates an estimated signal with the received physiological signal, a display device, wherein the prioritized OR module sends the received physiological signal to the display device as long as the received physiological signal is transmitted to the receiver, and further wherein when the estimation algorithm module calculates the estimated signal, and the wireless transmitter stops transmitting the received physiological signal to the receiver, the prioritized OR module sends the estimated signal to the display device.

DETAILED DESCRIPTION

Figure 1:
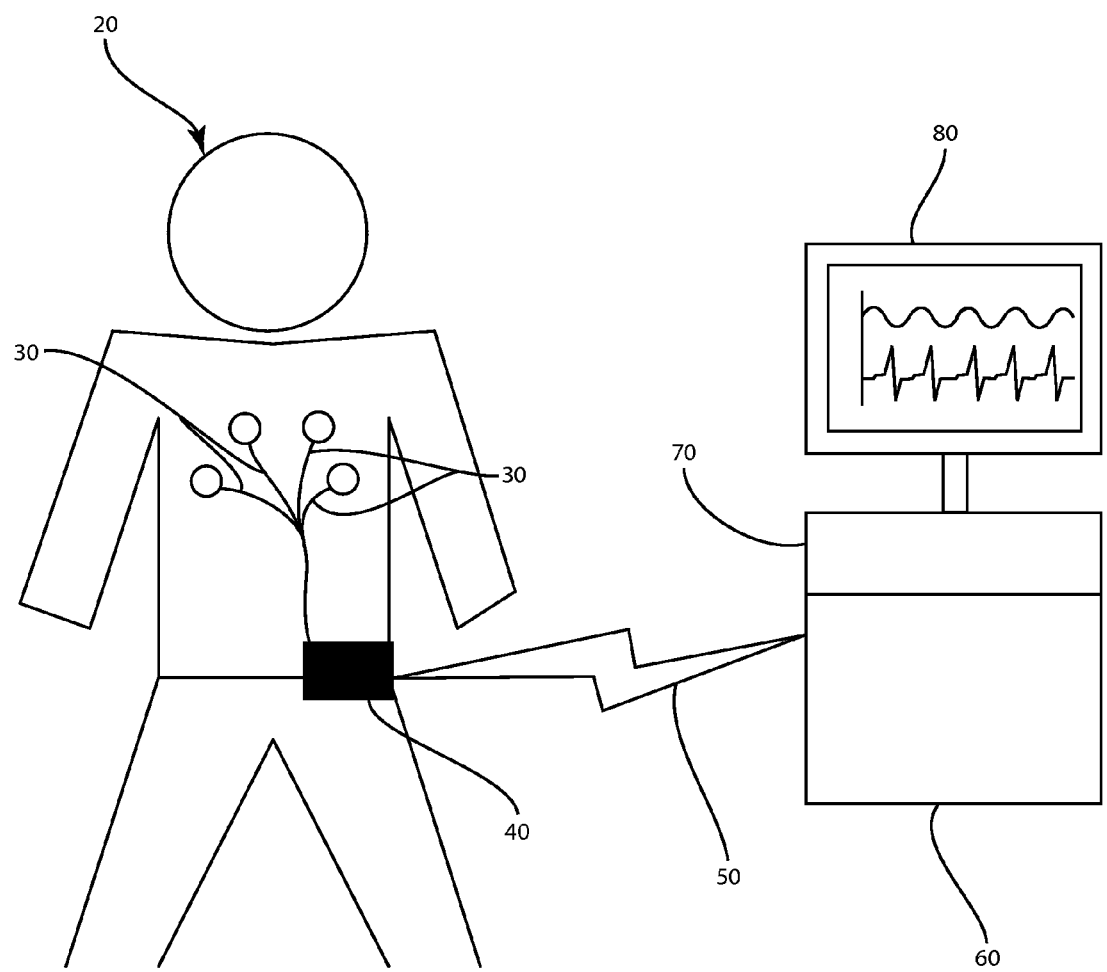
FIG. 1 is a graphical representation illustrating an embodiment of a system of the present application.

FIG. 1 illustrates an embodiment of the system 10 of the present application. Here, a patient 20 is being monitored for any number of physiological parameters and corresponding physiological signals are collected by an acquisition device 30. In FIG. 1, an ECG acquisition device 30 is illustrated. However, many types of physiological parameters and signals may be collected and transmitted wirelessly 50. A non-limiting list of possible monitored and collected physiological parameters includes not only an ECG signal, but also $SpO_2$, heart rate and/or respiratory rate. Further in the system 10 depicted in FIG. 1, a wireless transmitter 40 receives the physiological signals from the acquisition device 30 and transmits them wirelessly 50 to a receiver 60. The wireless transmitter 40 may be any such transmitter 40 that attaches to a patient, the patient's clothing, or even the patients bed, and transmits signals wirelessly. One non-limiting example of such a device is a biomedical telemetry device.

Still referring to FIG. 1, the receiver 60 relays the signal on to the display device 70 where the signal is buffered, and the signal image is displayed on the display monitor 80. As will be discussed in further detail below, the wireless transmitter 40 will transmit sampled, digitized values of the acquired signal wirelessly 50 to the receiver 60 until an estimation algorithm in each of the wireless transmitter 40 and the receiver 60 calculate an estimated signal for the acquired physiological parameters. When an estimated signal is made, the transmitter will refrain from sending new signal values, and the receiver 60 will then pass the estimated signal to the display device 70 for displaying on the display monitor 80. If the wireless transmitter 40 detects that the estimated signal exceeds an error range with respect to the actual acquired signal, it will immediately transmit the actual acquired signal value. The wireless transmitter may also send the actual value of all estimated samples acquired since the prior transmission. The error range is predetermined, and specific to the physiological parameter being monitored. In additional embodiments, the error range may be adjusted by a user.

Figure 2:
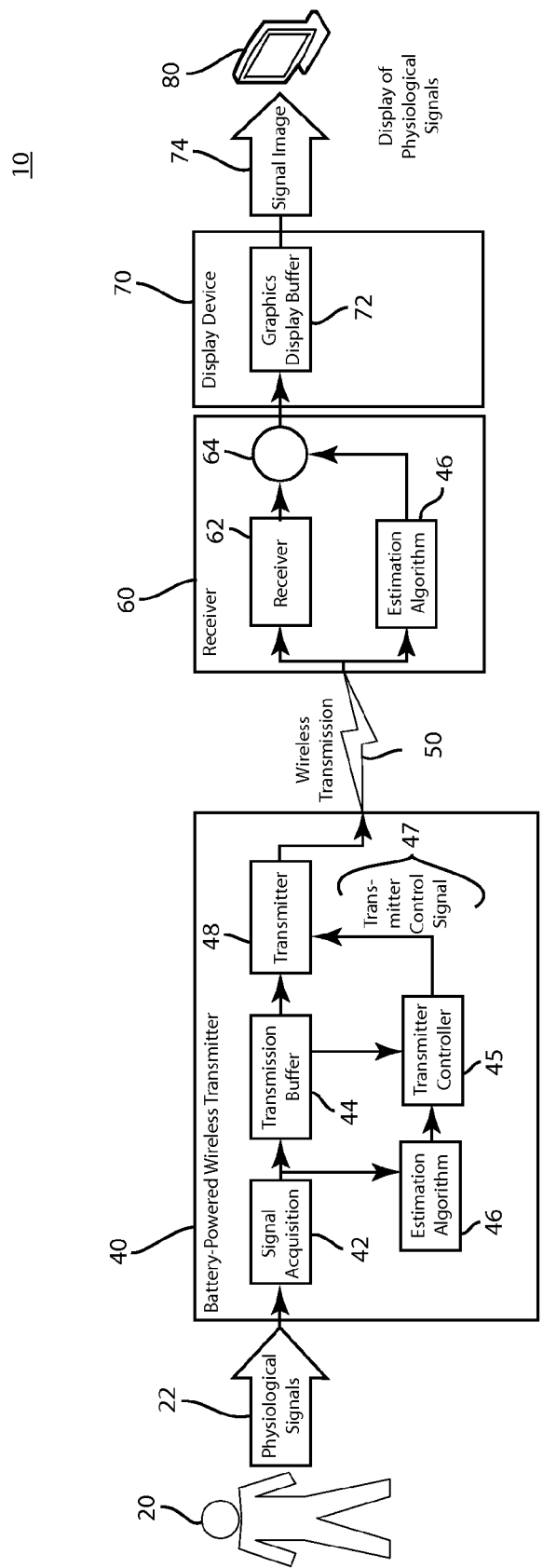
FIG. 2 is a schematic block diagram illustrating an embodiment of a system of the present application.

The system 10 is comprised of three basic parts as shown in FIG. 2. A wireless transmitter 40 acquires physiological signals 22 from a patient 20, and converts them to digital form and then wirelessly transmits 50 them to a receiver 60. The receiver 60 passes the wireless transmission 50 with minimal delay to a display 80. A display device 70 collects the signal data from the receiver 60 and forms a signal waveform image 74 to be displayed and viewed on the display 80.

Both the wireless transmitter 40 and the receiver 60 use an identical estimation algorithm in the estimation algorithm module 46 that predicts the physiological signals. As described above, the transmitter will transmit the acquired signal continuously for an initial period during which the estimation algorithm module calculates an estimation of new physiological signal samples. After this initialization period has passed, the wireless transmitter 40 compares the estimation to the actual acquired signal in real time. The wireless transmitter 40 buffers the data in the transmission buffer module 44 and only transmits it when the difference between estimated and actual values exceeds a predetermined error limit. Thus, as long as the difference between estimated and actual values remains within the predetermined error limit, the receiver 60 can send the estimation to the display 80 even though no data has been transmitted from the wireless transmitter 40 to the receiver 60. When the receiver 60 eventually receives actual collected data, it overwrites the estimated data in the memory of the receiver 60 (not shown), and the graphics display buffer 72 and displayed image on the display 80 are updated accordingly.

Still referring to FIG. 2, physiological signals 22 collected from the patient 20 are received in the signal acquisition module 42 of the wireless transmitter 40. The signal acquisition module 42 sends the physiological signals to both the transmission buffer 44 and the estimation algorithm module 46. The estimation algorithm module 46 may include a number of estimation algorithms for as many physiological parameters that may be collected by the wireless transmitter 40. The estimation algorithm module 46 may incorporate algorithms that are already utilized in the art to estimate future physiological signals based upon past physiological signals, or may include any later known estimation algorithms for calculating the same.

During initial start-up operation, the transmission buffer 44 sends the acquired signal to the transmitter 48 that wirelessly transmits 50 the acquired signal to the receiver 60, wherein the acquired signal is sent to the receiver module 62 and the estimation algorithm module 46. In the receiver 60, the prioritized OR 64 passes the acquired signal from the receiver 62 to the display device 70 unless the estimation algorithm module 46 has calculated an estimated signal. Once this occurs, the transmitter control signal 47 instructs the transmitter module 48 to stop transmitting the acquired signal. At this point in operation, there is no wireless transmission of a signal 50, and the receiver module 62 no longer has an acquired signal to send to the prioritized OR 64 and onto the display device 70. The estimation algorithm module 46 in the receiver 60 sends the estimated signal through the prioritized OR 64 and onto the display device 70.

Still referring to FIG. 2, when the transmitter controller 45 calculates that an error between the estimated signal and the actual acquired signal fall outside of a predetermined error range, then the transmitter controller 45 instructs the transmitter module 48 to start transmitting the acquired signal once again wirelessly 50 to the receiver 60. This transmitted acquired signal will then allow the receiver module 62 to send this through the prioritized OR 64 to the display device 70.

In the display device 70, a graphics display buffer 72 formats the signal for displaying, and outputs a signal image 74 to be displayed on the display monitor 80. As illustrated in FIG. 1, the receiver 60, display device 70 and display monitor 80 may be incorporated as one physical device or grouped or separated according to hardware configurations known in the art and the particular needs of certain applications.

It is also contemplated that there are various ways in which the display monitor 80 can indicate to the user that the signals presented on the display monitor 80 are estimated signals rather than acquired, real-time signals. In several embodiments of the present application, the physiological displays may be shaded, have a distinctive coloration, or include dots or dashes on the waveform or its background. This is not an exhaustive list of methods for which to distinguish the graphical display of the signal to illustrate to a user whether the signal is estimated or acquired. Of course, once the display monitor 80 reverts back to displaying a real-time acquired physiological signal, then this indicator would be removed and the physiological data updated and displayed accordingly.

It is also contemplated that the system 10 is equipped with a detector (not shown) that would detect the presence of a caregiver at the display monitor 80. For example, a non-exhaustive list of such options to detect the presence of a caregiver may be activation by the nurse call system installed in the patient's room, a close-motion detector installed in the display monitor 80 and/or a button on the display monitor 80 that a caregiver would depress when the caregiver is viewing the display monitor 80. Such detection device may override the estimation algorithm module 46 and allow the transmission of the acquired signals to the receiver 60 or may simply alter the frequency with which such acquired signal is transmitted and alternated with the estimated signal.

Still referring to FIG. 2, it should also be noted that each of the wireless transmitter 40 and the receiver 60 include a storage medium (not shown) for storing a set of computer-executable code, and a processor (not shown) for executing such code. The operation of each of the wireless transmitter 40 and receiver 60 is effectuated by the processing of such code by the processor.

Still referring to FIG. 2, in another embodiment of the system 10, only the receiver 60 includes an estimation algorithm module 46. In such an embodiment (not shown), the wireless transmitter 40 would not include the estimation algorithm module 46 or the transmitter controller 45, but instead would include a transmission buffer module 44 adapted to transmit the acquired signal for a predetermined period of time, and then rely upon the estimation algorithm module 46 in the receiver 60 to display an estimated signal on the display monitor 80. The transmission buffer module 44 of this additional embodiment would then stop transmitting the acquired signal after an additional predetermined period of estimated signal display. The frequency at which the transmission buffer module 44 switched from a transmission mode to an estimated mode may be preset by the manufacturer and/or adjusted by the user for particular applications and physiological parameters. This embodiment would not operate to transmit the acquired signal only when an error threshold was reached, but would ensure that an actual acquired signal was displayed in alternating segments with an estimated signal.

Figure 3:
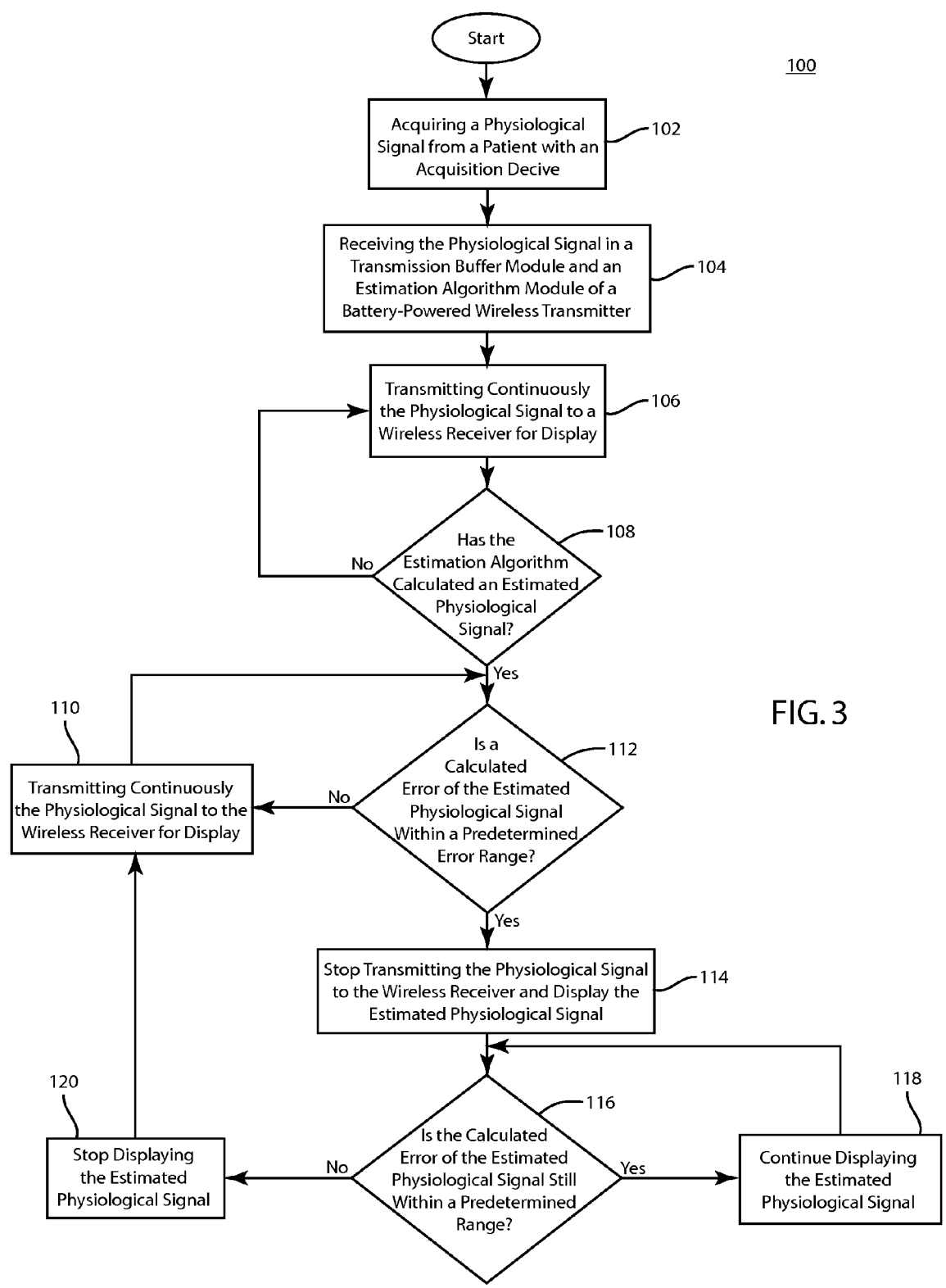
FIG. 3 is a flowchart illustrating an embodiment of a method of the present application.

Now referring to FIG. 3, a method 100 of the present application is illustrated. In step 102, a physiological signal is acquired from a patient with an acquisition device. In step 104, the physiological signal is received in a transmission buffer module and an estimation algorithm module of a wireless transmitter. In step 106, the physiological signal is continuously transmitted to a wireless receiver for display. In choice 108, if the estimation algorithm has not yet calculated an estimated physiological signal, then this physiological signal continues to be transmitted to the wireless receiver for display in step 106. Still in 108, if the estimated algorithm has indeed calculated an estimated physiological signal, then in step 112, it is determined whether the calculated error of the estimated physiological signal is within a predetermined error range. If not, then in step 110, the physiological signal is transmitted continuously to the wireless receiver for display. If in 112 the error of the estimated physiological signal is within a predetermined error range, then in step 114 the method 100 stops transmitting the physiological signal to the wireless receiver and displays the estimated physiological signal. In 116, if the calculated error of the estimated physiological signal is still within a predetermined range, then the estimated signal is displayed continuously in step 118. If the calculated error of the estimated physiological signal in 116 is not within a predetermined range, then the estimated signal is no longer displayed in step 120, and the physiological signal is transmitted continuously to the wireless receiver for display in step 110.

In a system described by this invention, practical limitations exist. For example, the wireless transmitter cannot buffer data and hold off communication with the receiver indefinitely, even if the estimation remains within the error limit. It is necessary in such cases for the wireless transmitter and receiver to implement a fail-safe mechanism to detect the possible loss of a communication channel, thereby preventing the display of inaccurate data for an unacceptable time period. This fail-safe mechanism could be implemented as a time-out function or another means. The wireless transmitter must transmit a message when a predetermined length of time has passed since the previous transmission to avoid triggering the fail-safe mechanism.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A wireless physiological signal transmission and display system, the system comprising:
    a wireless transmitter in close proximity to a patient, the wireless transmitter including a transmission buffer module, and a first estimation algorithm module, wherein the wireless transmitter receives a physiological signal collected from the patient and calculates a first estimated signal with the first estimation algorithm module and compares the first estimated signal with the received physiological signal in real time;
    a receiver including a second estimation algorithm and a prioritized OR module, wherein the wireless transmitter wirelessly transmits the received physiological signal to the receiver and the second estimation algorithm module calculates a second estimated signal with the received physiological signal;
    a display device, wherein the prioritized OR module sends the received physiological signal to the display device as long as the received physiological signal is transmitted to the receiver, and further wherein when the first estimation algorithm module calculates the first estimated signal, and the first estimated signal is within a predetermined error range of the received physiological signal, the wireless transmitter stops transmitting the received physiological signal to the receiver, and the prioritized OR module sends the second estimated signal to the display device.

2. The system of claim 1, wherein when the first estimated signal exceeds the predetermined error range, the wireless transmitter resumes transmitting the received physiological signal to the receiver and the prioritized OR sends the received physiological signal to the display device.

3. The system of claim 1, wherein the display device overwrites the second estimated signal with the received physiological signal on a display monitor and in a storage medium when the prioritized OR sends the received physiological signal to the display device.

4. The system of claim 1, wherein the first and second estimation algorithm modules utilize an identical algorithm for calculating the first and second estimated signals.

5. The system of claim 1, further comprising an acquisition device, wherein the acquisition device collects the physiological signal from the patient.

6. The system of claim 5, wherein the wireless transmitter includes a signal acquisition module, wherein the signal acquisition module receives the physiological signal from the acquisition device and sends the physiological signal to the transmission buffer module and the first estimation algorithm module.

7. The system of claim 1, wherein a transmitter controller sends a transmitter control signal to a transmitter module when the first estimated signal is within the predetermined error range.

8. The system of claim 1, wherein the receiver includes a receiver module that receives the physiological signal from the wireless transmitter and sends the physiological signal to the prioritized OR.

9. The system of claim 1, wherein the display device includes a graphics display buffer, wherein the graphics display buffer converts the received physiological signal or the second estimated signal into a signal waveform image and sends the signal waveform image to the display monitor.

10. The system of claim 9, wherein the signal waveform image has a first line format when the received physiological signal is being displayed on the display monitor and a second line quality when the second estimated signal is being displayed on the display monitor.

11. A method of wireless physiological signal transmission and display, the method comprising:
receiving a physiological signal collected from a patient with a wireless transmitter in close proximity to the patient, the wireless transmitter including a transmission buffer module, and a first estimation algorithm module;
calculating a first estimated signal with the first estimation algorithm module;
comparing the first estimated signal with the received physiological signal in real time;
wirelessly transmitting the received physiological signal to a receiver including a second estimation algorithm and a priority OR module;
calculating a second estimated signal in the second estimated algorithm with the received physiological signal;
sending the received physiological signal to a display device with the prioritized OR as long as the received physiological signal is transmitted to the receiver, wherein when the first estimation algorithm module calculates the first estimated signal, and the first estimated signal is within a predetermined error range of the received physiological signal, the wireless transmitter stops transmitting the received physiological signal to the receiver, and the prioritized OR module sends the second estimated signal to the display device.

12. The method of claim 11, further comprising resuming transmitting the received physiological signal to the receiver with the wireless transmitter and sending with the prioritized OR the received physiological signal to the display device, when the first estimated signal exceeds the predetermined error range.

13. The method of claim 11, further comprising overwriting the second estimated signal with the received physiological signal on a display monitor and in a storage medium with the display device when the prioritized OR sends the received physiological signal to the display device.

14. The method of claim 11, wherein the first and second estimation algorithm modules utilize an identical algorithm for calculating the first and second estimated signals.

15. The method of claim 11, further comprising collecting the physiological signal from the patient with an acquisition device.

16. The method of claim 15, wherein the wireless transmitter includes a signal acquisition module, wherein the signal acquisition module receives the physiological signal from the acquisition device and sends the physiological signal to the transmission buffer module and the first estimation algorithm module.

17. The method of claim 11, further comprising sending a transmitter control signal to a transmitter module when the first estimated signal is within the predetermined error range with a transmitter controller.

18. The method of claim 11, wherein the receiver includes a receiver module that receives the physiological signal from the wireless transmitter and sends the physiological signal to the prioritized OR.

19. The method of claim 11, further comprising converting the received physiological signal or the second estimated signal into a signal waveform image and sending the signal waveform image to the display monitor with a graphics display buffer in the display device.

20. The method of claim 19, wherein the signal waveform image has a first line format when the received physiological signal is being displayed on the display monitor and a second line quality when the second estimated signal is being displayed on the display monitor.

21. A wireless physiological signal transmission and display system, the system comprising:
a wireless transmitter in close proximity to a patient, the wireless transmitter including a transmission buffer module, wherein the wireless transmitter receives a physiological signal collected from a patient;
a receiver including an estimation algorithm and a prioritized OR module, wherein the wireless transmitter wirelessly transmits the received physiological signal to the receiver and the estimation algorithm module calculates an estimated signal with the received physiological signal;
a display device, wherein the prioritized OR module sends the received physiological signal to the display device as long as the received physiological signal is transmitted to the receiver, and further wherein when the estimation algorithm module calculates the estimated signal, and the wireless transmitter stops transmitting the received physiological signal to the receiver, the prioritized OR module sends the estimated signal to the display device.

22. The system of claim 21, wherein the wireless transmitter resumes transmitting the received physiological signal to the receiver and the prioritized OR sends the received physiological signal to the display device, further wherein the resumed transmission is made by a wireless transmitter periodically.

* * * * *